(12) United States Patent
Thom et al.

(10) Patent No.: US 10,238,880 B2
(45) Date of Patent: Mar. 26, 2019

(54) MEDICAL DEVICES HAVING DEFORMABLE STRUCTURES PROVIDING MEDICAL LEAD FIXATION

(71) Applicant: MEDTRONIC, INC., Minneapolis, MN (US)

(72) Inventors: Andrew J. Thom, Maple Grove, MN (US); Rajesh V. Iyer, Eden Prairie, MN (US); Darren A. Janzig, Lindstrom, MN (US); Randy S. Roles, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/939,613

(22) Filed: Nov. 12, 2015

(65) Prior Publication Data
US 2016/0129267 A1 May 12, 2016

Related U.S. Application Data

(60) Provisional application No. 62/078,746, filed on Nov. 12, 2014.

(51) Int. Cl.
*A61N 1/375* (2006.01)
*A61N 1/36* (2006.01)

(52) U.S. Cl.
CPC ......... *A61N 1/3752* (2013.01); *A61N 1/3605* (2013.01)

(58) Field of Classification Search
CPC .... A61N 1/3605; A61N 1/375; A61N 1/3752; A61N 1/3968

USPC .............................. 607/2, 36, 37, 115, 116
See application file for complete search history.

(56) References Cited

U.S. PATENT DOCUMENTS

| | | |
|---|---|---|
| 4,328,813 A | 5/1982 | Ray |
| 4,672,979 A | 6/1987 | Pohndorf |
| 4,995,389 A | 2/1991 | Harris |
| 5,354,326 A | 10/1994 | Comben et al. |
| 5,489,225 A | 2/1996 | Julian |
| 5,545,188 A * | 8/1996 | Bradshaw ............ A61N 1/3752 607/37 |
| 5,951,595 A | 9/1999 | Moberg |
| 6,044,304 A | 3/2000 | Baudino |
| 6,134,477 A | 10/2000 | Knuteson |
| 6,210,417 B1 | 4/2001 | Baudino et al. |
| 6,356,792 B1 | 3/2002 | Errico et al. |

(Continued)

FOREIGN PATENT DOCUMENTS

| | | |
|---|---|---|
| CN | 202236888 | 5/2012 |
| DE | 4232627 A1 | 4/1993 |

(Continued)

OTHER PUBLICATIONS

PCT/US2015/060394 International Search Report and Written Opinion dated Feb. 22, 2016.

(Continued)

*Primary Examiner* — Michael Carey
(74) *Attorney, Agent, or Firm* — Withers & Keys, LLC

(57) ABSTRACT

Medical devices include deformable structures that contact a lead upon being compressed. A grip that a clinician may grasp and manipulate is engaged with a nose structure of a header block of the medical device, and manipulation of the grip causes compression of the deformable structure to ultimately create fixation of the lead within the header block.

44 Claims, 16 Drawing Sheets

(56) References Cited

U.S. PATENT DOCUMENTS

| | | |
|---|---|---|
| 6,428,368 B1 * | 8/2002 | Hawkins .............. A61N 1/3752 439/271 |
| 6,430,442 B1 | 8/2002 | Peters et al. |
| 6,473,654 B1 | 10/2002 | Chinn |
| 7,580,756 B2 | 8/2009 | Schulte et al. |
| 7,981,119 B2 | 7/2011 | Lando et al. |
| 7,988,674 B2 | 8/2011 | Adams et al. |
| 7,993,352 B2 | 8/2011 | Black et al. |
| 8,182,540 B2 | 5/2012 | Lin et al. |
| 8,355,786 B2 | 1/2013 | Malinowski |
| 8,355,787 B2 | 1/2013 | Barker |
| 8,556,860 B2 | 10/2013 | Stratton et al. |
| 8,738,151 B2 | 5/2014 | Nelson |
| 9,283,372 B2 | 3/2016 | Bondhus |
| 9,919,145 B2 | 3/2018 | Bondhus |
| 2002/0143376 A1 | 10/2002 | Chinn et al. |
| 2004/0230268 A1 | 11/2004 | Huff et al. |
| 2007/0250077 A1 | 10/2007 | Skakoon et al. |
| 2009/0264943 A1 | 10/2009 | Barker |
| 2010/0029127 A1 * | 2/2010 | Sjostedt .............. H01R 13/59 439/346 |
| 2011/0022100 A1 | 1/2011 | Brase et al. |
| 2012/0035616 A1 | 2/2012 | Olsen et al. |
| 2012/0083867 A1 | 4/2012 | Wahlstrand et al. |
| 2012/0157924 A1 | 6/2012 | Schutz et al. |
| 2012/0259386 A1 | 10/2012 | DeRohan et al. |
| 2013/0204336 A1 | 8/2013 | Sharma et al. |
| 2014/0273602 A1 | 9/2014 | Bondhus |
| 2015/0119964 A1 | 4/2015 | Janzig |
| 2016/0193458 A1 | 7/2016 | Bondhus |
| 2016/0129267 A1 | 12/2016 | Thom |

FOREIGN PATENT DOCUMENTS

| | | |
|---|---|---|
| EP | 2497527 | 12/2012 |
| WO | 2018/102042 | 6/2018 |

OTHER PUBLICATIONS

U.S. Appl. No. 14/212,091 dated Feb. 24, 2016 Issue Notification.
U.S. Appl. No. 14/212,091 dated Feb. 16, 2016 Response to Amendment Under Rule 312.
U.S. Appl. No. 14/212,091 dated Jan. 29, 2016 Amendment After Notice of Allowance (Rule 312).
U.S. Appl. No. 14/212,091 dated Oct. 29, 2015 Notice of Allowance.
U.S. Appl. No. 14/212,091 dated Sep. 29, 2015 Amendment/Reconsideration.
U.S. Appl. No. 14/212,091 dated Jun. 29, 2015 Non-Final Rejection.
U.S. Appl. No. 15/070,808 dated Oct. 19, 2017 Response.
U.S. Appl. No. 15/070,808 dated Oct. 2, 2017 Advisory Action.
U.S. Appl. No. 15/070,808 dated Sep. 19, 2017 Response.
U.S. Appl. No. 15/070,808 dated Jul. 19, 2017 Final Rejection.
U.S. Appl. No. 15/070,808 dated Jun. 21, 2017 Amendment/Reconsideration.
U.S. Appl. No. 15/070,808 dated Mar. 21, 2017 Non-Final Rejection.
U.S. Appl. No. 15/070,808 dated Mar. 6, 2017 Response to Restriction.
DBS/Advance, DBS Extensions with eXtend Technology, St. Jude Medical, 2011.
Written Opinion and Search Report for PCT/US2017/057348, dated Feb. 2, 2018.

* cited by examiner

MEDICAL DEVICES HAVING DEFORMABLE STRUCTURES PROVIDING MEDICAL LEAD FIXATION

TECHNICAL FIELD

Embodiments relate to medical devices that receive medical leads. More particularly, embodiments relate to medical devices that include deformable structures to provide fixation of the medical leads that have been inserted into the medical devices.

BACKGROUND

Medical devices that provide a medical function such as electrical stimulation are often affixed to the body at a position of convenience. This is particularly true for implantable medical devices where the device is implanted in a convenient location that may be some distance from a target site within the body where the medical therapy is to be applied. A medical lead is attached to the medical device and is routed to the target site within the body.

The medical lead for electrical stimulation provides electrical contacts on a proximal end and electrodes on a distal end with conductors inside a lead body where those conductors interconnect proximal contacts to distal electrodes that are in contact with the body tissue. The lead is typically attached to the medical device by the proximal end of the lead being inserted into a bore within a header block of the medical device. The proximal contacts of the lead become electrically coupled to electrical connectors within the header block so that stimulation signals pass from the electrical connectors to the proximal contacts and then through the conductors to the distal electrodes.

To fix the lead within the bore, a set screw within a set screw block of the header block is tightened onto a metal ring on the proximal end of the medical lead that is present within the bore of the header block. While the set screw adequately fixes the position of the proximal end of the lead within the bore of the header block, using a set screw for lead fixation presents some drawbacks. For instance, in most cases a clinician must use a tool to tighten the set screw because the set screw cannot be adequately gripped and because the set screw becomes countersunk within the set screw block as the set screw is tightened. Furthermore, the set screw presents a connection that potentially exposes the interior of the header block to fluid ingress.

SUMMARY

Embodiments address issues such as these and others by providing a medical device that includes a grip and a deformable structure to establish lead fixation. When the grip is manipulated, a compression force is applied to the deformable structure which then applies a radial force to the proximal end of the lead within the header bore. Thus, the deformable structure provides fixation of the lead within the header block. In one or more embodiments, the deformable structure may also provide a sealing function to prevent the ingress of fluids around the lead and into the header bore.

Embodiments provide a method of fixing a proximal end of medical lead into a bore of a medical device. The method involves inserting the proximal end of the medical lead into the bore. The method further involves transferring force from a grip that is movable relative to the bore to a deformable structure constrained relative to the bore by the medical device to cause compression of the deformable structure so that the deformable structure engages the lead within the bore to fix the position of the lead as the deformable structure compresses.

Embodiments provide a medical device that includes a header block having a bore with an engagement surface and a plurality of electrical connectors within the bore. The medical device also includes a grip mechanically engaged with the engagement surface of the header block. Additionally, the medical device includes a deformable structure that is constrained by the header block, the deformable structure providing a compression force in a radial direction of the bore when a force is applied from the grip to the deformable structure.

Embodiments provide a medical system that includes a medical device having a stimulation circuit and a header block. The header block has a bore with an engagement surface and a plurality of electrical connectors within the bore that are electrically coupled to the stimulation circuit. The medical device further includes a grip mechanically engaged with the engagement surface of the header block and also includes a deformable structure that is constrained by the header block. The deformable structure provides a compression force in a radial direction of the bore when a force is applied from the grip to the deformable structure. The medical system includes a medical lead that has a lead body surrounding electrical conductors, the lead body having a proximal region positioned within the bore of the header block. The proximal region has a plurality of contacts that engage corresponding electrical connectors in the bore and engage the conductors within the lead body. The deformable structure is compressed into contact with a portion of the proximal region of the medical lead to fix the medical lead within the bore.

DETAILED DESCRIPTION

Embodiments provide medical devices with a grip mechanically engaged with a header block and a deformable structure within a bore of the header block. Manipulation of the grip results in compression of the deformable structure which causes the deformable structure to apply force radially relative to the bore so as to contact a proximal region of the lead that is present within the bore. The force being applied by the deformable structure to the proximal region of the lead results in fixation of the lead within the bore of the header block.

Figure 1:
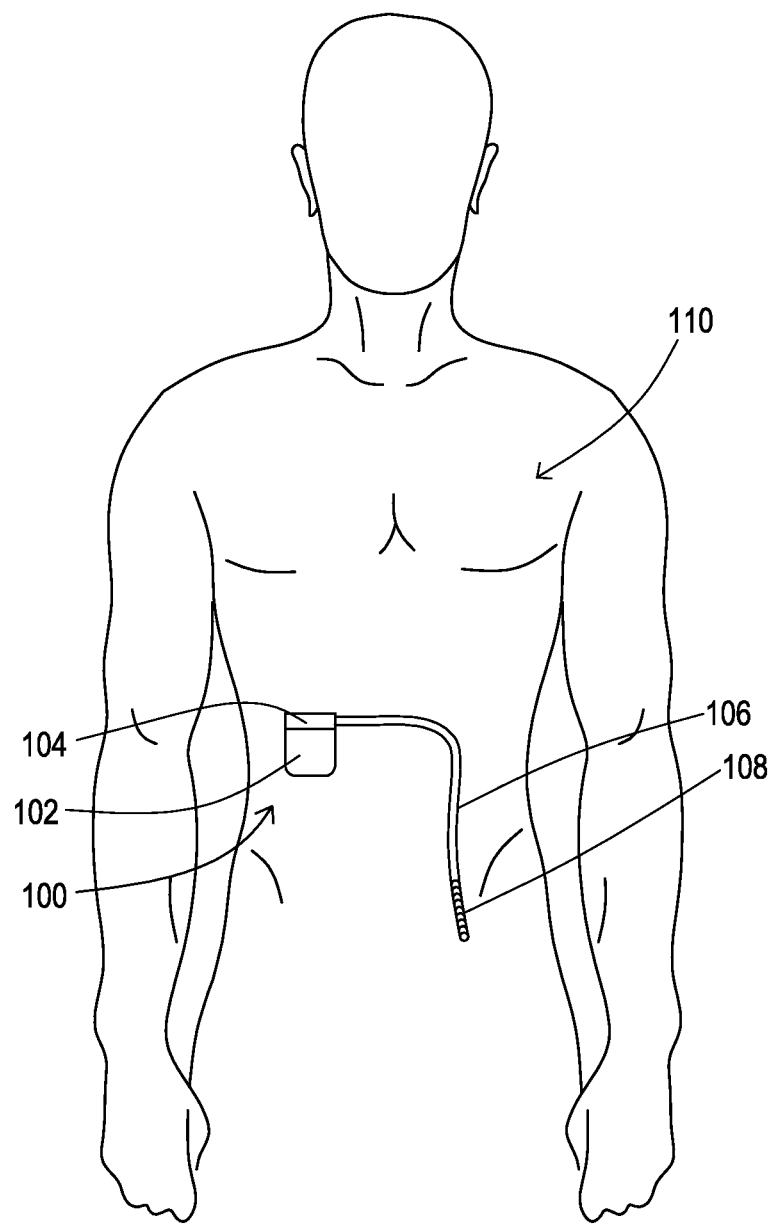
FIG. 1 shows an operating environment for various embodiments where a medical system including a medical device and a medical lead are attached to or implanted into a patient.

FIG. 1 shows a medical system 100 that includes a medical device 102 and a medical lead 106. In this particular example, the medical system 100 including the medical device 102 and the medical lead 106 are implantable. The medical lead 106 includes a proximal end that has been inserted into a bore of a header block 104 of the medical device 102. The distal end of the medical lead 106 includes electrodes 108 that are positioned at a target site where electrical stimulation therapy is to be provided.

Figure 2A:
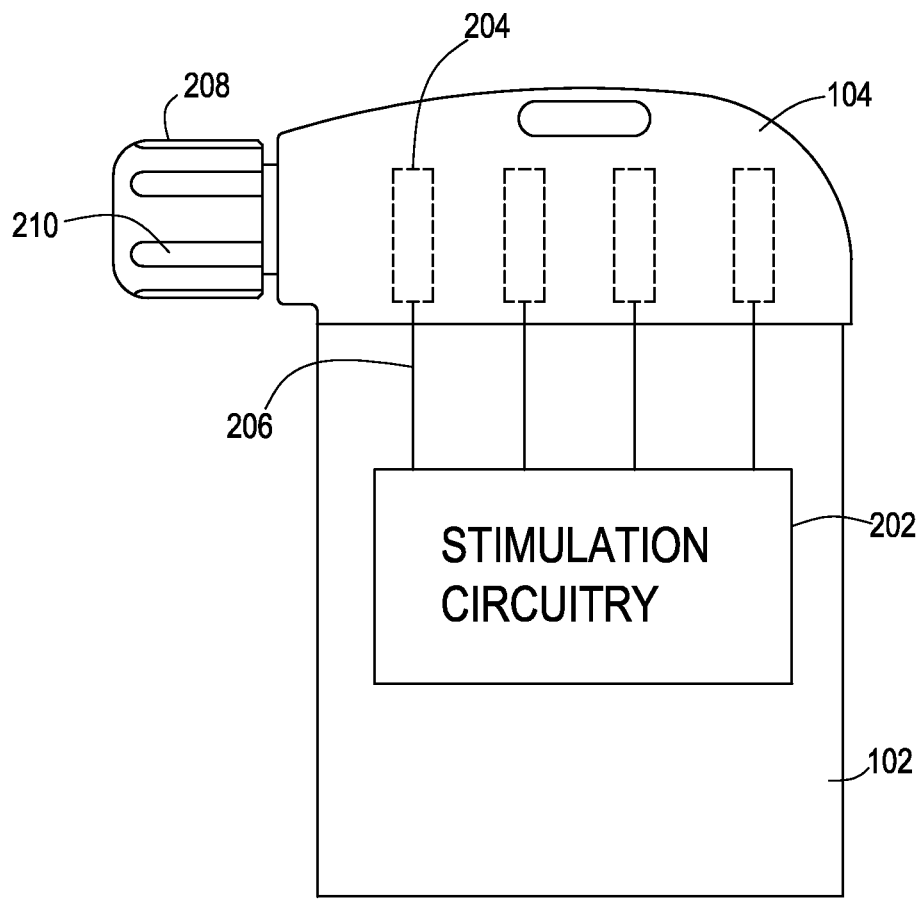
FIG. 2A shows an example of a medical device having a grip that can be manipulated to provide lead fixation.

FIG. 2A shows an example of the medical device 102 and a header block 104 of the medical device 102. The header block 104, as well as the header blocks of the other figures that are discussed herein, may be a separate assembly that is mounted to the medical device 102 or may be integral to the medical device 102 via a common housing. The medical device 102 of this example includes stimulation circuitry 202 that provides electrical stimulation signals via a set of feed through conductors 206 that interconnect with corresponding electrical connectors 204 inside of the header block 104. The medical device 102 of this example also includes a grip 208 that can be grasped and manipulated by a clinician, and thus by hand and without tools, when connecting a lead 106 to the header block 104 of the medical device 102.

Figure 2B:
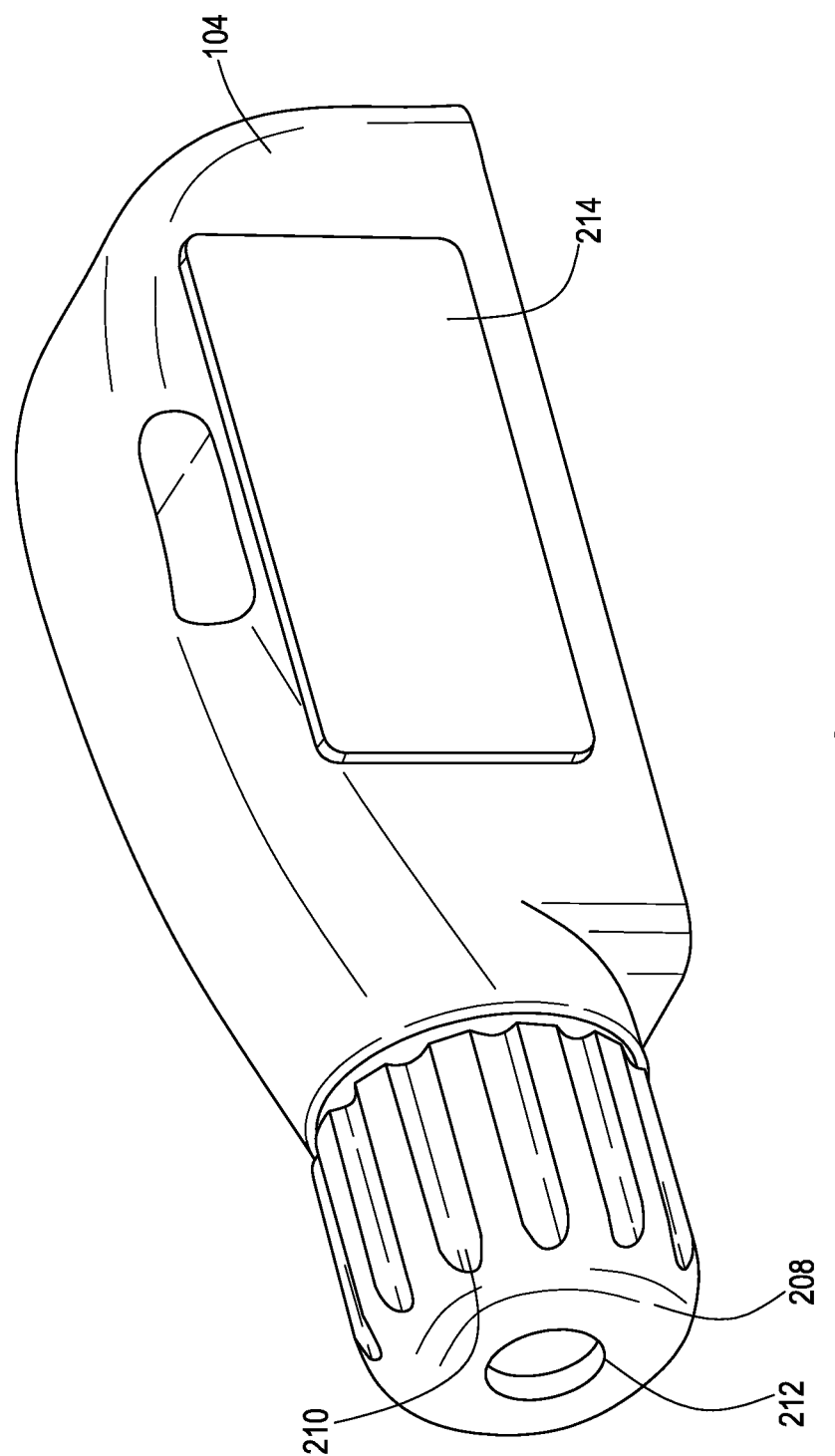
FIG. 2B shows a perspective view of a header block and an associated grip.

The header block 104 and grip 208 are also shown in the perspective view of FIG. 2B. As can be seen in FIGS. 2A and 2B, the grip 208 may include grooves 210 or other knurled like surface treatments to provide additional friction that aids in grasping and manipulating the grip 208. The grip 208 is movable relative to the header block 104 which allows the grip 208 to be manipulated to provide fixation of the lead 106 that has been inserted into a bore 212 of the grip 208 of this example that leads to the bore of the header block 104. Examples of manipulation of the grip 208 to provide fixation for the lead 106 are discussed below with reference to FIGS. 3-6. In this example, the header block 104 includes a cover 214 that may be installed on to the header block 104 after the internal features of the header block 204 such as electrical connectors and seals are positioned and surrounded with a filler material.

Figure 3A:
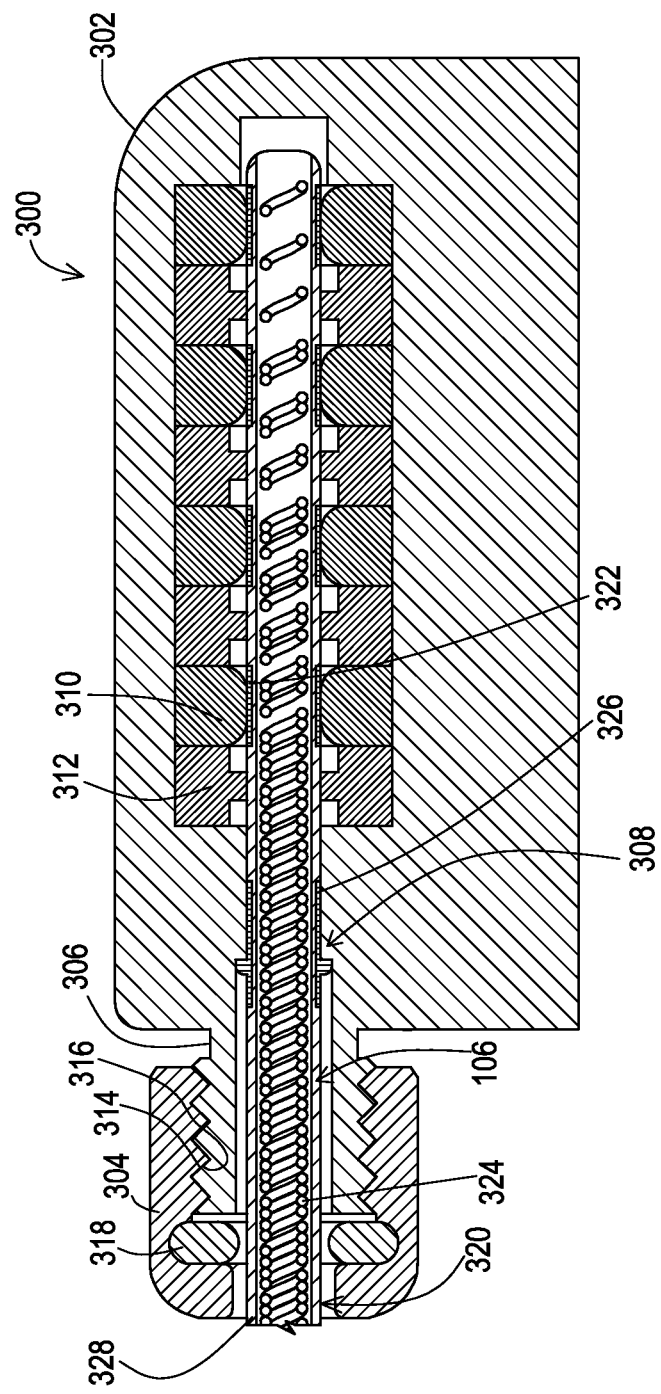
FIG. 3A shows a cross-sectional view of a first example of a grip and an associated header block that has a deformable structure that provides fixation to a medical lead within the header block.

FIG. 3A shows a cross-sectional view of an example of a header block 300 with a design that utilizes a deformable structure for lead fixation. The header block 300 includes a housing 302, and within the housing 302 a bore 308 is defined by a nose structure 306 affixed or integral to the housing 302 and a series of interleaved seals 312 and electrical connectors 310. A proximal end of the lead 106 has been inserted into a bore 320 of a grip 304 and further into the bore 308 of the remainder of the header block 300. The electrical connectors 310 make physical contact with electrical contacts 322 of the lead 106, and conductors 324 of the lead 106 are electrically coupled with corresponding electrical contacts 322 such that the conductors 324 are electrically coupled with the connectors 310. The conductors 324 extend to the distal end of the lead 106 (not shown in FIG. 3A) where they are electrically coupled to corresponding electrodes 108.

In this example, the lead 106 includes a ring 326 that has a flange that provides a hard stop for the lead 106 within the bore 308. Conventionally, a set screw would be tightened against this ring 326 to fix the position of the lead 106, but in this example the set screw has been eliminated. Instead, the nose structure 306 is provided with an engagement surface 316, which in this example is an exterior threaded surface, and the grip 304 is likewise provided with an interior threaded surface 314 that threads onto the surface 316. Therefore, the grip 304 in this example acts as a nut that tightens against the nose structure 306 when turned a given direction.

A deformable structure 318, which in this example is an elastomeric O-ring, is positioned between a blunt end of the nose structure 306 and an internal surface of the grip 304. As the grip 304 is manipulated by being turned in the tightening direction, the grip 304 moves toward the nose structure 306 and therefore compresses the deformable structure 318. The deformable structure 318 then deforms so as to shrink in the direction of movement of the grip 304 but to grow in a direction perpendicular to the direction of movement of the grip 304 which is a radial direction of the bore 308.

Figure 3B:
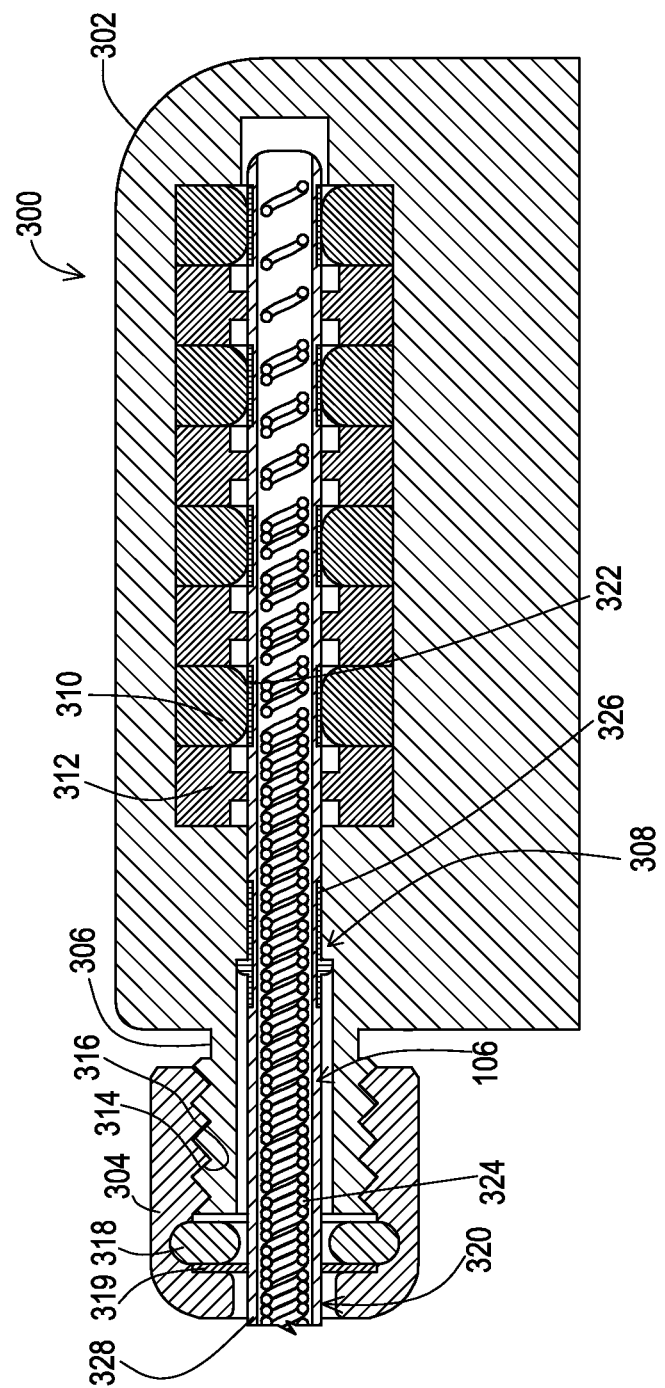
FIG. 3B shows a cross-sectional view of the first example of a grip and an associated header block that has a deformable structure that provides fixation to a medical lead within the header block but further includes a washer that abuts the grip.

Because the surface of the grip 304 that applies the force to the deformable structure 318 is turning, a washer 319 which is shown in FIG. 3B may be positioned between the inner surface of the grip 304 and the deformable structure 318. The turning surface of the grip 304 contacts the washer 319 rather than directly contacting the deformable structure 318 to lessen any chance of damaging the deformable structure 318 due to the motion of the grip 304.

By growing in the radial direction of the bore 308, the deformable structure 318 creates a force in that radial direction by pressing against the lead 106. In this example, the deformable structure 318 presses directly against a lead body 328 of the lead 106. It will be appreciated that a metal ring could be placed about the lead body in the position where the deformable structure 318 makes contact if so desired, or may make contact with the ring 326 as discussed in other embodiments below. This force against the lead 106 creates a high degree of friction between the deformable structure 318 and the lead body 328 which provides fixation of the lead 106 within the header block 300. Additionally, the pressure of the deformable structure against the lead 106 presents a seal to restrict fluid ingress. Another advantage is that in some cases, the deformable structure 318 may have some degree of axial movement further urging the lead body 328 into the fully inserted position within the header block 300, such as where a ridge on the ring 326 becomes fully seated against a hard stop in the header block 300.

Various materials may be used for the various objects of the header 300 of FIGS. 3A and 3B. The deformable structure may be constructed of various materials that provide the deformable characteristic, such as silicone. The grip 304 may be constructed of materials including metals such as titanium, niobium, or titanium-niobium alloys, and the like as well as other materials including rigid polymers that are biocompatible. The housing 302 and the nose structure 306, which may be integral or may be established as two or more coupled pieces, may also be constructed of various materials, including the same materials noted above for the grip 304. The electrical connectors and seals may be constructed of materials that are used for these items in conventional header block designs.

Figure 4:
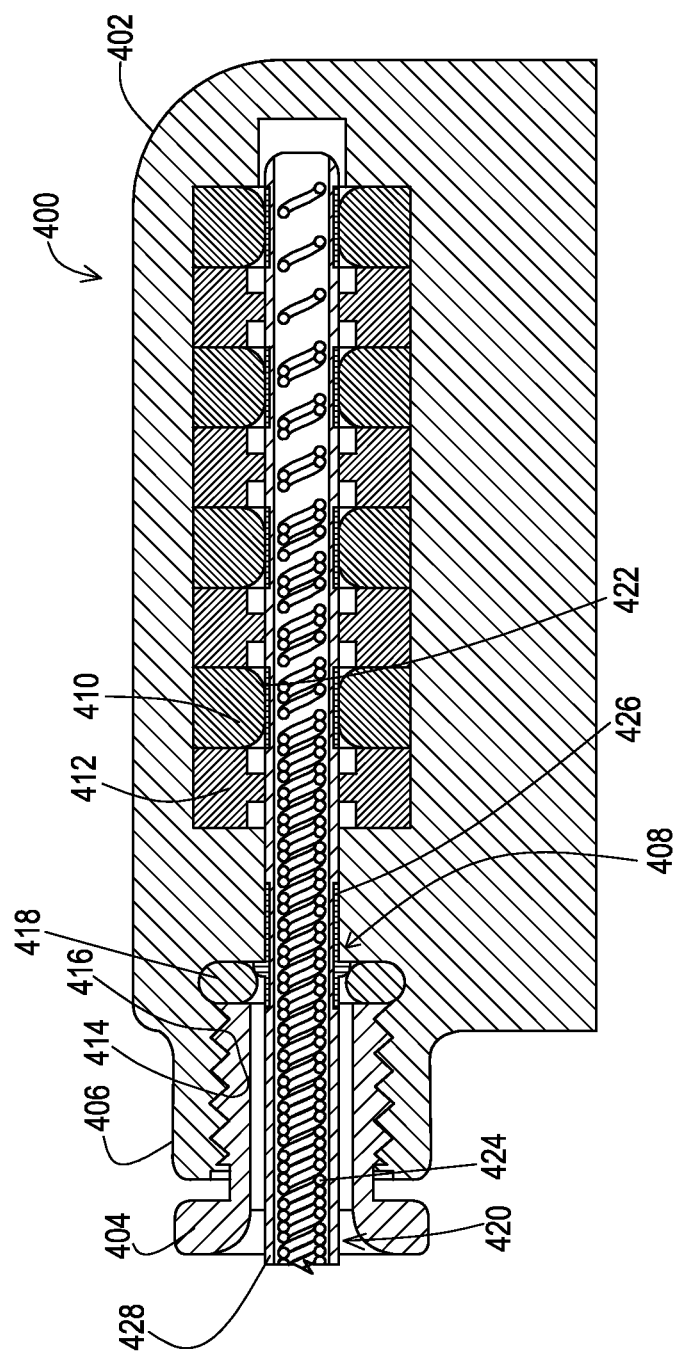
FIG. 4 shows a cross-sectional view of a second example of a grip and an associated header block that has a deformable structure that provides fixation to a medical lead within the header block.

FIG. 4 shows a cross-sectional view of a second example of a header block 400 with a design that utilizes a deformable structure for lead fixation. The header block 400 includes a housing 402, and within the housing 402 a bore 408 is defined by a nose structure 406 affixed or integral to the housing 402 and a series of interleaved seals 412 and electrical connectors 410. A proximal end of the lead 106 has been inserted into a bore 420 of a grip 404 and further into the bore 408 of the remainder of the header block 400. The electrical connectors 410 make physical contact with electrical contacts 422 of the lead 106, and conductors 424 of the lead 106 are electrically coupled with corresponding electrical contacts 422 such that the conductors 424 are electrically coupled with the connectors 410. The conductors 424 extend to the distal end of the lead 106 (not shown in FIG. 4) where they are electrically coupled to corresponding electrodes 108.

In this example, the lead 106 includes a ring 426 that has a flange that provides a hard stop for the lead 106 within the bore 408. As discussed above in relation to FIG. 3A, conventionally, a set screw would be tightened against this ring 426 to fix the position of the lead 106, but in this example the set screw has been eliminated. Instead, the nose structure 406 is provided with an engagement surface 414, which in this example is an interior threaded surface, and the grip 404 is likewise provided with an exterior threaded surface 416 that threads onto the surface 414. Therefore, the grip 404 in this example acts as a nut that tightens against the nose structure 406 when turned a given direction.

A deformable structure 418, which in this example is an elastomeric O-ring, is positioned between a blunt end of the grip 404 and an internal surface of the nose structure 406. As the grip 404 is manipulated by being turned in the tightening direction, the grip 404 moves toward the nose structure 406 and therefore compresses the deformable structure 418. The deformable structure 418 then deforms so as to shrink in the direction of movement of the grip 404 but to grow in a direction perpendicular to the direction of movement of the grip 404 which is a radial direction of the bore 408. Because the blunt end of the grip 404 that applies the force to the deformable structure 418 is turning, a washer, like washer 319 discussed above in relation to FIG. 3B may be positioned between the blunt end of the grip 404 and the deformable structure 418. In that case, the turning surface of the grip contacts the washer rather than directly contacting the deformable structure 418 to lessen any chance of damaging the deformable structure 418 due to the motion of the grip 404.

By growing in the radial direction of the bore 408, the deformable structure 418 creates a force in that radial direction by pressing against the lead 106. In this example, the deformable structure 418 presses against the metal ring 426 of the lead 106, but it will be appreciated that the deformable structure 418 may be positioned to contact the lead body directly instead. This force against the lead 106 creates a high degree of friction between the deformable structure 418 and the ring 426 which provides fixation of the lead 106 within the header block 400. Additionally, the pressure of the deformable structure against the lead 106 presents a seal to restrict fluid ingress.

As with the header block 300 of FIGS. 3A and 3B, the items of the header block 400 may also be constructed of various materials. Indeed, the same materials listed for the items of the header block 300 may also be used for those items within the header block 400.

Figure 5A:
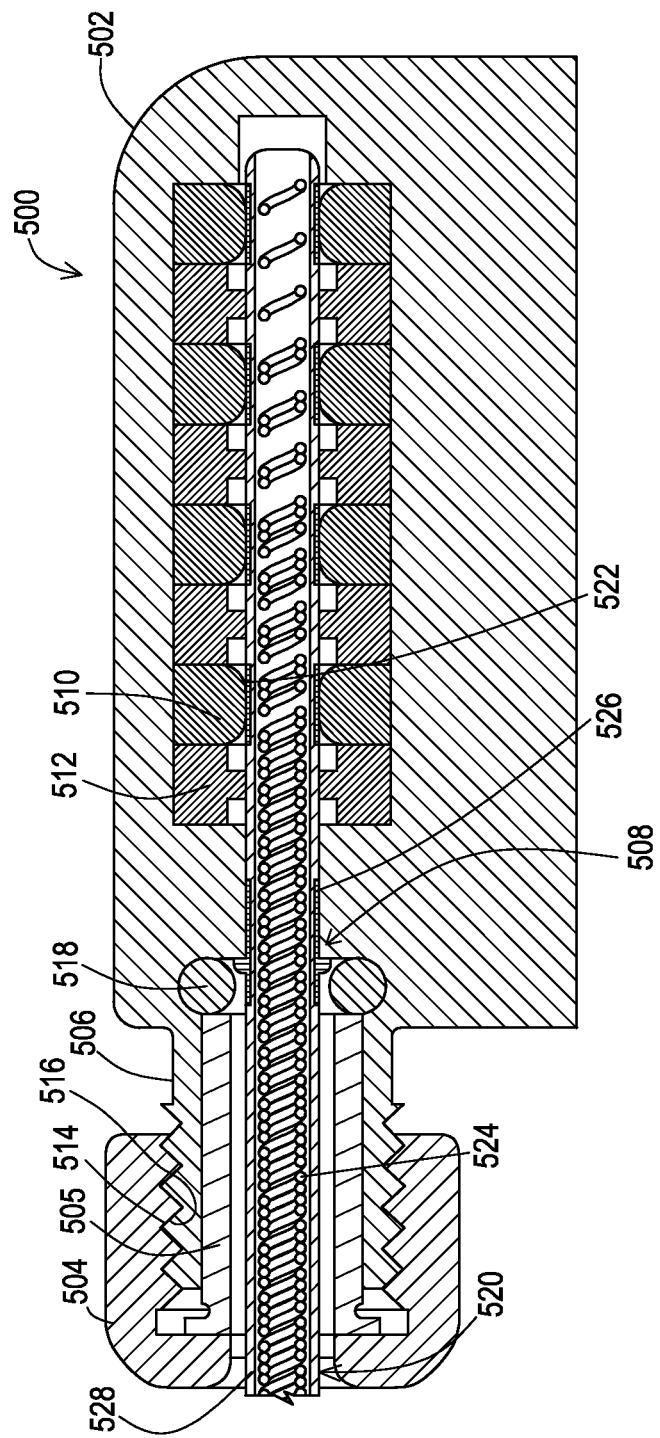
FIG. 5A shows a cross-sectional view of a third example of a grip and an associated header block that has a deformable structure that provides fixation to a medical lead within the header block.

FIG. 5A shows a cross-sectional view of a third example of a header block 500 with a design that utilizes a deformable structure for lead fixation. The header block 500 includes a housing 502, and within the housing 502 a bore 508 is defined by a nose structure 506 affixed or integral to the housing 502 and a series of interleaved seals 512 and electrical connectors 510. A proximal end of the lead 106 has been inserted into a bore 520 of a grip 504 and further into the bore 508 of the remainder of the header block 500. The electrical connectors 510 make physical contact with electrical contacts 522 of the lead 106, and conductors 524 of the lead 106 are electrically coupled with corresponding electrical contacts 522 such that the conductors 524 are electrically coupled with the connectors 510. The conductors 524 extend to the distal end of the lead 106 (not shown in FIG. 5A) where they are electrically coupled to corresponding electrodes 108.

In this example, the lead 106 includes a ring 526 that has a flange that provides a hard stop for the lead 106 within the bore 508. As discussed above in relation to FIGS. 3 and 4, conventionally, a set screw would be tightened against this ring 526 to fix the position of the lead 106, but in this example the set screw has been eliminated in this example. Instead, the nose structure 506 is provided with an engagement surface 516, which in this example is an exterior threaded surface, and the grip 504 is likewise provided with an interior threaded surface 514 that threads onto the surface 516. Therefore, the grip 504 in this example acts as a nut that tightens against the nose structure 506 when turned a given direction.

In this example, a ferrule 505 is positioned within the bore of the nose structure 506 and the lead 106 passes through the ferrule 505. The ferrule 505 contacts an inner surface of the grip 504 such that movement of the grip 504 as the grip is manipulated forces the ferrule 505 to also move.

A deformable structure 518, which in this example is an elastomeric O-ring, is positioned between a blunt end of the ferrule 505 and an internal surface of the nose structure 506. As the grip 504 is manipulated by being turned in the tightening direction, the grip 504 moves toward the nose structure 506 and therefore moves the ferrule 505 toward the deformable structure 516 to compress the deformable structure 518. The deformable structure 518 then deforms so as to shrink in the direction of movement of the grip 504 but to grow in a direction perpendicular to the direction of movement of the grip 504 which is a radial direction of the bore 508. Because the blunt end of the grip 504 is turning but is against the ferrule 505, there is no contact of the turning grip 504 to the deformable structure. The ferrule 505 provides a similar affect to including a washer between the grip 504 and the deformable structure 518 as discussed above in relation to FIG. 3B.

By growing in the radial direction of the bore 508, the deformable structure 518 creates a force in that radial direction by pressing against the lead 106. In this example, the deformable structure 518 presses against the metal ring 526 of the lead 106, but it will be appreciated that the deformable structure 518 may be positioned to contact the lead body directly instead. This force against the lead 106 creates a high degree of friction between the deformable structure 518 and the ring 526 which provides fixation of the lead 106 within the header block 500. Additionally, the pressure of the deformable structure against the lead 106 presents a seal to restrict fluid ingress.

The ferrule 505 may have a collar as shown on the left side of the ferrule 505 that eventually abuts the blunt end of the nose structure 506 to act as a stop. The deformable structure 518 will be creating pressure against the lead 106 at level adequate to fix the lead 106 position within the header block 500 just prior to the collar of the ferrule 505 reaching the nose structure 506. By having the collar of the ferrule 505 contact the nose structure 506, over compression of the deformable structure 518 that might cause damage is prevented.

Figure 5B:
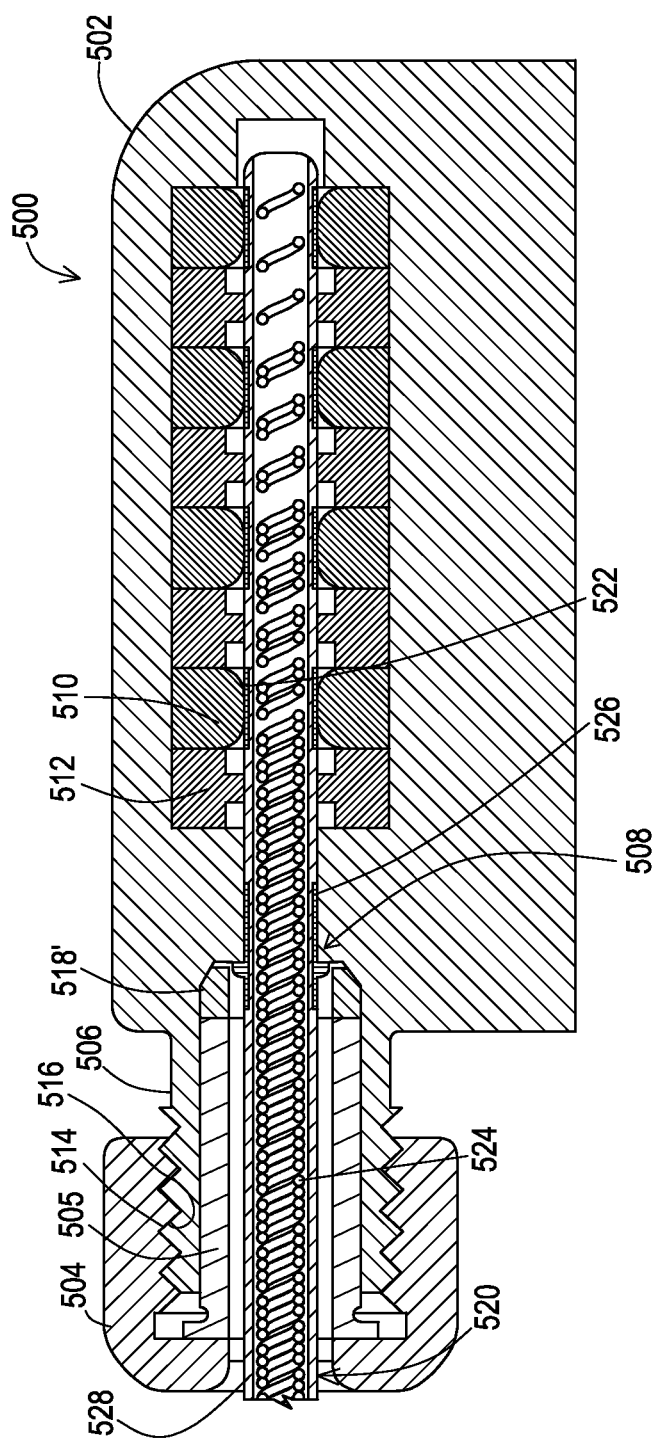
FIG. 5B shows a cross-sectional view of a fourth example of a grip and an associated header block that has a deformable structure that provides fixation to a medical lead within the header block.

FIG. 5B shows a cross-sectional view of a fourth example where the header block 500 and most components may be the same as from the third example in FIG. 5A. However, rather than utilizing a deformable structure 518 of FIG. 5A that has the round or oval cross-section, a deformable structure 518' is utilized that has a conical cross-section. The internal surface of the housing 502 provides a matching conical surface to which the conical surface of the deformable structure 518' makes contact. As the ferrule 505 is forced against the deformable structure 518', the deformable structure 518' is forced to achieve a smaller inside diameter.

This decreased inner diameter results in the deformable structure 518' making contact with the lead 106, and in this example, contacting the ring 526. This contact creates the lead fixation. The deformable structure 518' may be of various forms such as a metallic O-ring. This metallic O-ring may be coated or electroplated to allow better adhesion and to provide a ductile surface for better sealing against the lead body. As discussed above for the example of FIG. 5A, the ferrule 505 may have a collar on the left side that eventually abuts the blunt end of the nose structure to prevent over compression of the deformable structure 518'.

As with the header block 300 of FIG. 3A, the items of the header block 500 of FIGS. 5A and 5B may also be constructed of various materials. Indeed, the same materials listed for the items of the header block 300 may also be used for those items within the header block 500. Further, the ferrule 505 of the header block 500 may be constructed of various materials well, such as titanium, niobium, titanium-niobium alloys, MP35N® alloy (Ni—Co—Cr—Mo alloy), stainless steel and the like.

Figure 6A:
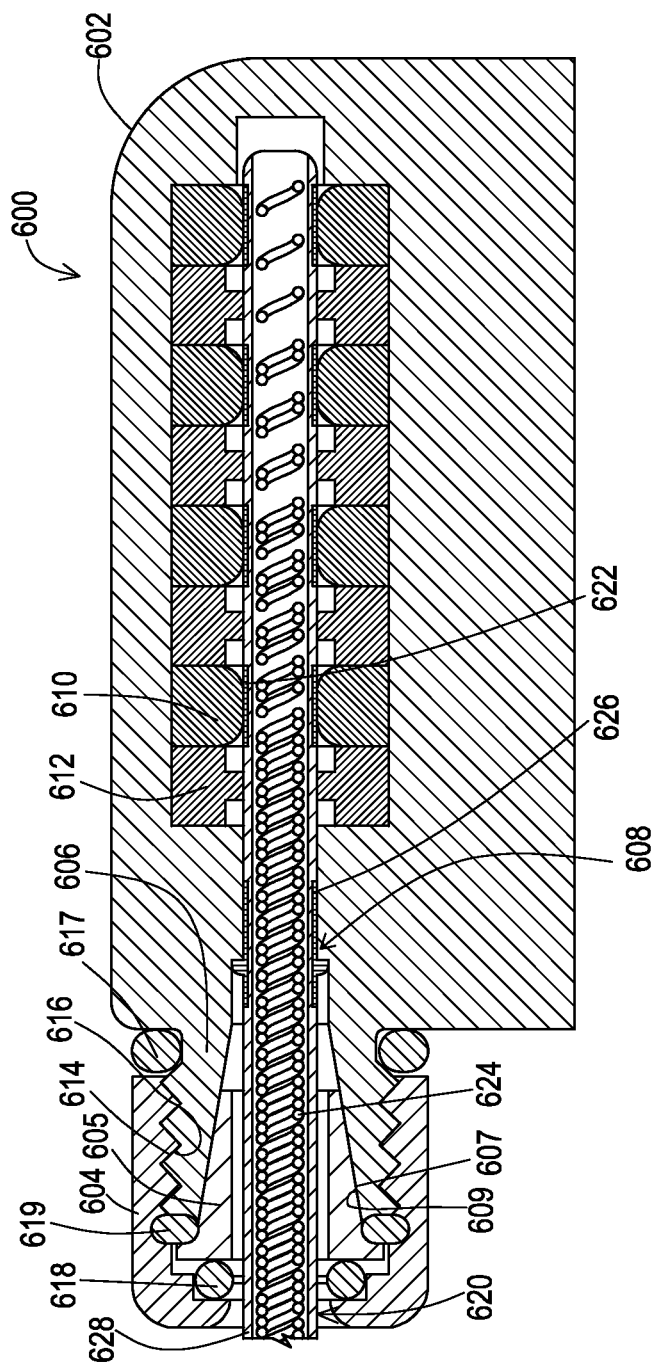
FIG. 6A shows a cross-sectional view of a fifth example of a grip and an associated header block that has a deformable structure that provides fixation to a medical lead within the header block.

FIG. 6A shows a cross-sectional view of an example of a header block 600 with a design that utilizes a deformable structure for lead fixation. The header block 600 includes a housing 602, and within the housing 602 a bore 608 is defined by a nose structure 606 affixed or integral to the housing 602 and a series of interleaved seals 612 and electrical connectors 610. A proximal end of the lead 106 has been inserted into a bore 620 of a grip 604 and further into the bore 608 of the remainder of the header block 600. The electrical connectors 610 make physical contact with electrical contacts 622 of the lead 106, and conductors 624 of the lead 106 are electrically coupled with corresponding electrical contacts 622 such that the conductors 624 are electrically coupled with the connectors 610. The conductors 624 extend to the distal end of the lead 106 (not shown in FIG. 6A) where they are electrically coupled to corresponding electrodes 108.

In this example, the lead 106 includes a ring 626 that has a flange that provides a hard stop for the lead 106 within the bore 608. Conventionally, a set screw would be tightened against this ring 626 to fix the position of the lead 106, but in this example the set screw has been eliminated. Instead, the nose structure 606 is provided with an engagement surface 616, which in this example is an exterior threaded surface, and the grip 604 is likewise provided with an interior threaded surface 614 that threads onto the surface 616. Therefore, the grip 604 in this example acts as a nut that tightens against the nose structure 606 when turned a given direction.

In this example, a deformable structure 605 that is a conical structure is positioned within the conical bore 607 of the nose structure 606 and the lead 106 passes through the conical structure 605. The conical structure 605 contacts an inner surface of the grip 604 such that movement of the grip 604 as the grip is manipulated forces the conical structure 605 to also move. Because the conical bore 607 of the nose structure 606 engages a conical surface 609 of the conical structure 605, as the conical structure 605 moves, the conical structure 605 begins to deform where a diameter of the conical structure 605 begins the decrease.

As the diameter of the bore through the conical structure 605 decreases, the conical structure begins to compress onto the lead 106. In this example, the conical structure 605 presses directly against a lead body 628 of the lead 106. This force against the lead 106 creates a high degree of friction between the conical structure 605 and the lead body 628 which provides fixation of the lead 106 within the header block 600. Because the conical structure 605 presents a relatively large amount of surface area in contact with the lead body 628 compared with an O-ring of the prior embodiments, the force is distributed over a relatively large surface area of the lead body 628 which lessens the likelihood of such pressure cause damage to the lead body 628.

One or more additional deformable structures may also be included. In this example of FIG. 6A, three additional deformable structures 617, 618, and 619 are included in the form of elastomeric O-rings. One deformable structure 617 is positioned between the blunt end of the grip 604 and a shoulder of the housing 602. Another deformable structure 618 is positioned between an internal surface of the grip 604 and a blunt end of the conical structure 605. The other deformable structure 619 is positioned between a flange of the conical structure 605 and a blunt end of the nose structure 606. As the grip 604 is manipulated by being turned in the tightening direction, the grip 604 moves toward the nose structure 606, the housing 602, and the deformable structure 618, and this movement of the grip 604 in turn compresses the deformable structures 617 and 618 while also moving the flange of the conical structure 605 toward the deformable structure 619 to compress the deformable structure 619. The deformable structures 617, 618, and 619 then deform so as to shrink in the direction of movement of the grip 604 but to grow in a direction perpendicular to the direction of movement of the grip 604 which is a radial direction of the bore 608.

By growing in the radial direction of the bore 608, the deformable structure 618 creates a force in that radial direction by pressing against the lead 106 while the deformable structure 617 presses against the nose structure 606. This may provide an additional sealing function. The deformable structure 619 creates a force in the radial direction by pressing against the conical structure 605, and this may also provide an additional sealing function.

Figure 6B:
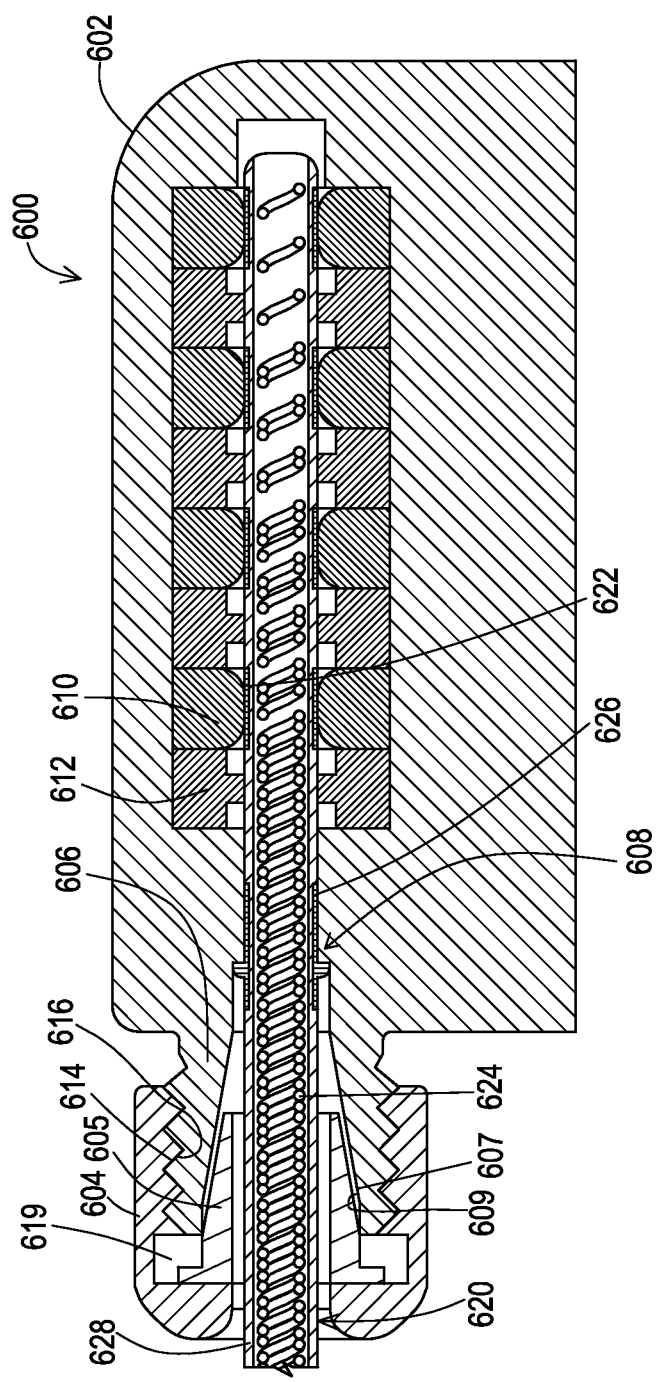
FIG. 6B shows a cross-sectional view of the fifth example of a grip and an associated header block that has a deformable structure that provides fixation to a medical lead within the header block but omits the additional sealing features.

The example of FIG. 6B shows the header block 600 without the additional deformable structures 617, 618, and 619. In this example, it can be seen that the grip 604 directly contacts the blunt end of the conical structure 605. There remains a gap between the flange and the nose structure 606 and there remains a gap between the end of the grip 604 and the shoulder of the housing 602.

Figure 6C:
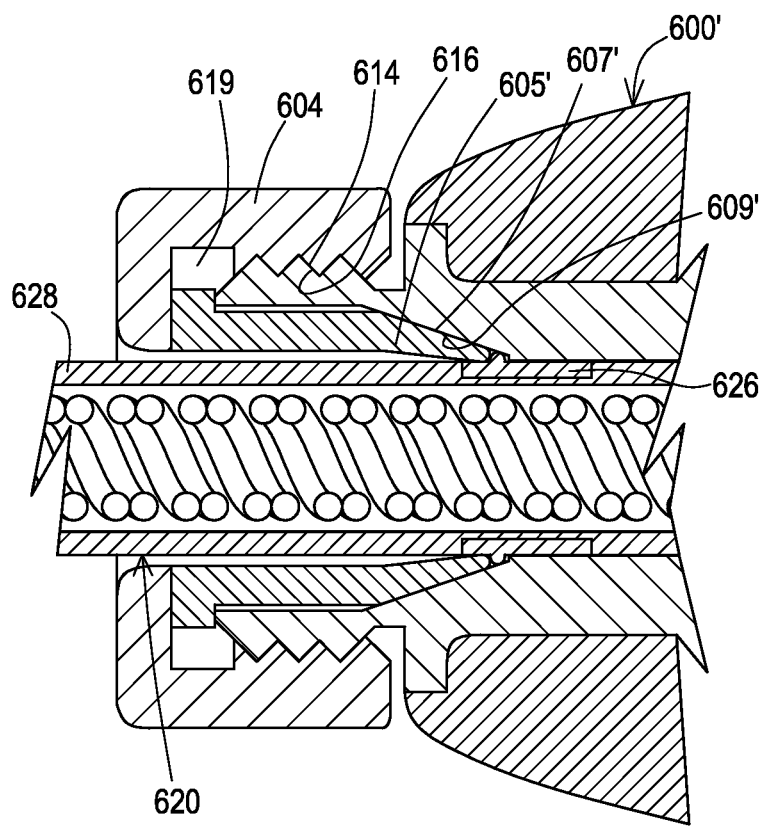
FIG. 6C shows a cross-sectional view of a sixth example of a grip and an associated header block that has a deformable structure that provides fixation to a medical lead within the header block but omits the additional sealing features but creates fixation against a metal ring on the lead.

The example of FIG. 6C shows a header block 600' that includes a conical surface 609' where the slope of the conical surface 609' extends down to the point where the ring 626 is present. Thus, as the grip 604 is moved toward the header block 600' such as by turning the grip 604, the slope of the conical structure 605' engages the slope of the conical surface 609' thereby causing the conical structure 605' to be forced toward and eventually contact the ring 626. This contact against the ring 626, which is typically a rigid material such as a biocompatible metal, provides fixation of the lead 628 within the header block 600' without the conical structure 605' contacting the lead body that is typically a polymer that is softer than the ring 626.

As with the header block 300 of FIG. 3, the items of the header block 600, 600' of FIGS. 6A-6C may also be constructed of various materials. Indeed, the same materials listed for the items of the header block 300 may also be used for those items within the header block 600, 600'. Further, the conical structure 605 of the header block 600, 600' may be constructed of various materials as well, such as titanium, niobium, titanium-niobium alloys, and the like. While the conical structure 605, 605' deforms to some degree to make contact with the lead 106 and/or metal ring 626, the conical structure 605, 605' may be constructed of metal because slits in the cone may be provided to allow the cone to deform to a smaller diameter.

Figure 7:
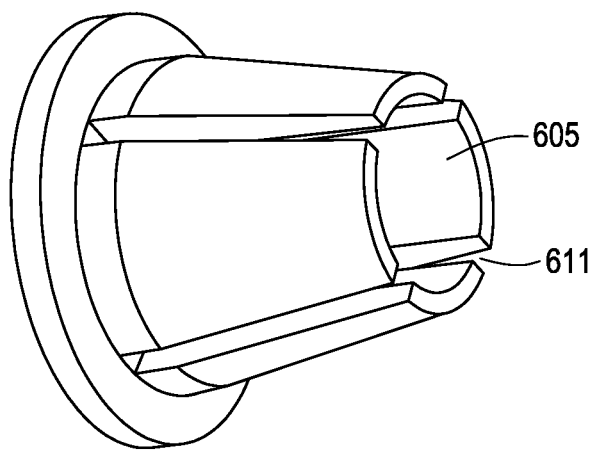
FIG. 7 shows an example of a deformable conical structure that may be utilized with one or more embodiments to provide lead fixation.

FIG. 7 shows an example of the conical structure 605. The slits 611 can be seen. These slits allow the conical structure to deform by being compressed to the smaller diameter inner bore.

In these prior examples, the grip has been described as providing a function like a nut by being threaded onto matching threads on the nose structure. However, other forms of the grip are also possible for these various examples that may or may not include threads. Likewise, the nose structure of these examples may or may not utilize threads. For instance, the grip could have other structures that lock to structures of the nose structure upon a clinician manipulating the grip by forcing the grip to move toward the nose structure, which in turn causes the deformation of the deformable structure that creates contact with the lead to provide fixation of the lead within the header block.

Other modifications are also possible. For example, the header blocks 300, 400, 500, and 600 discussed above are shown as having a single lead bore and therefore a single lead fixation configuration of the grip and deformable structure. However, it will be appreciated that header blocks 300, 400, 500 and 600 may be provided with multiple lead bores where a grip and deformable structure is provided for each bore so that each lead may be individually fixed in place and removed by manipulation of the corresponding grip.

Figure 8:
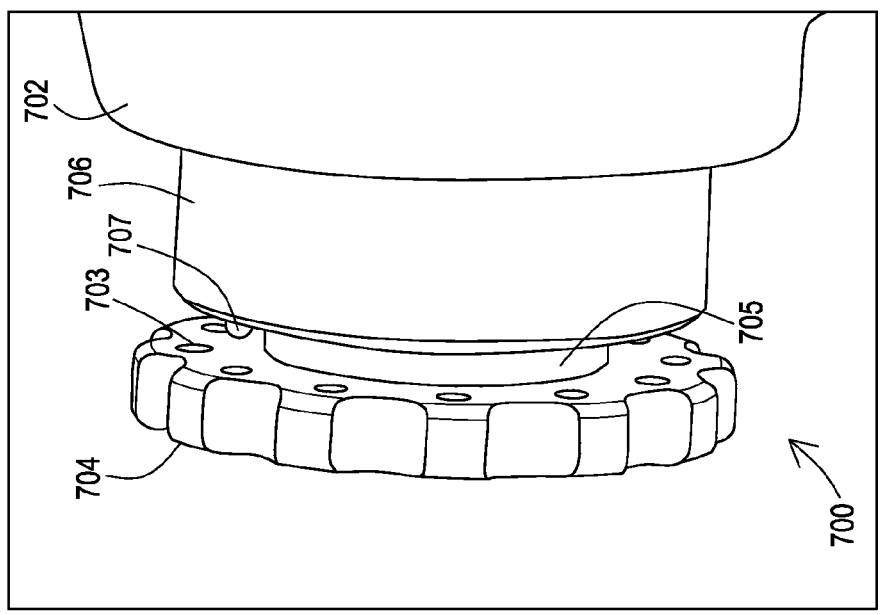
FIG. 8 shows a perspective view of a sixth example of a grip and an associated header block including first and second mating structures to lock the grip in a tightened state to maintain fixation of a medical lead provided by a deformable structure.
Figure 9:
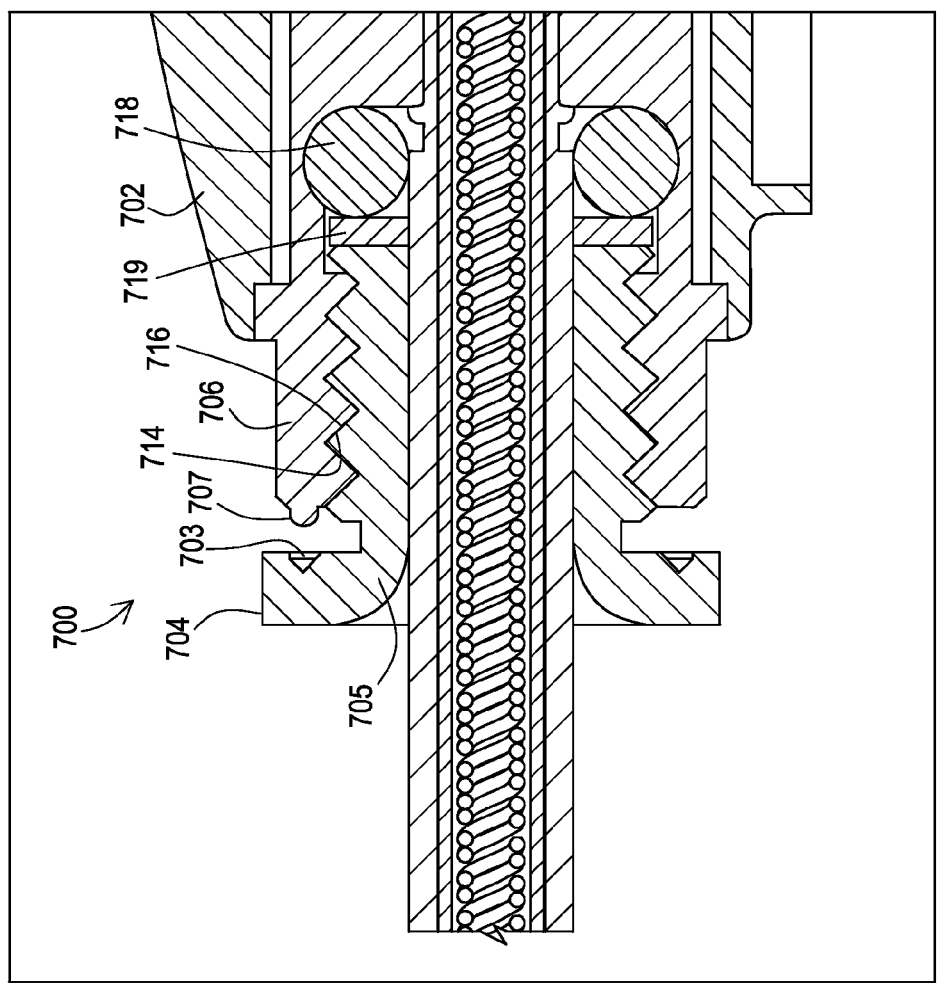
FIG. 9 shows a cross-sectional view of the sixth example.

FIGS. 8 and 9 show a seventh example of a grip 704 and header block 700 having a housing 702. As with the prior examples, the header block 700 includes a deformable structure 718 within a bore. In this example a washer 719 is present so that the grip 704 does not turn directly against the deformable structure 718, but in other embodiments the washer 719 may be omitted. Also in this example, the grip includes a shaft portion 705 having a threaded surface 714 while a nose structure 706 of the header block 700 includes a threaded surface 716 that engages the threaded surface 714 to allow the grip 704 to be turned to screw the grip 704 further into the bore and to apply force to the deformable structure 718.

To ensure that grip 704 maintains a tightened position to deform the structure 718 and provide fixation to the medical lead, mating structures such as holes 703 and a detent 707 are provided on the grip 704 and on the header block 700, respectively. In the example shown, the holes 703 of the grip 704 are provided on the radial surface of the grip 704 that faces the header block 700. These holes 703 may pass through the grip 704 or may be only a partial depth. In this example, the detent 707 is present on the nose structure 706 of the header block 700 and faces toward the grip 704. Once the grip 704 is tightened, the detent 707 engages a particular hole 703 which prevents the grip 704 from turning during normal use but may be turned when force is being applied by a user.

While a single detent 707 is shown, it will be appreciated that multiple detents may be present and may be spaced in correspondence with the spacing of the holes 703. Additionally, the position of the detent(s) 707 and the holes 703 may instead be swapped where the detent(s) 707 are present on the radial surface of the grip 704 while the holes 703 are present on the nose structure 706. The grip 704 and the nose structure 706 including the detent 707 may be constructed of the same materials as discussed above for other embodiments. It will be further appreciated that the use of mating structures such as holes and detents of FIGS. 8 and 9 may be applied to the prior examples to lock the grip in place and maintain the fixation of the lead.

Figure 10A:
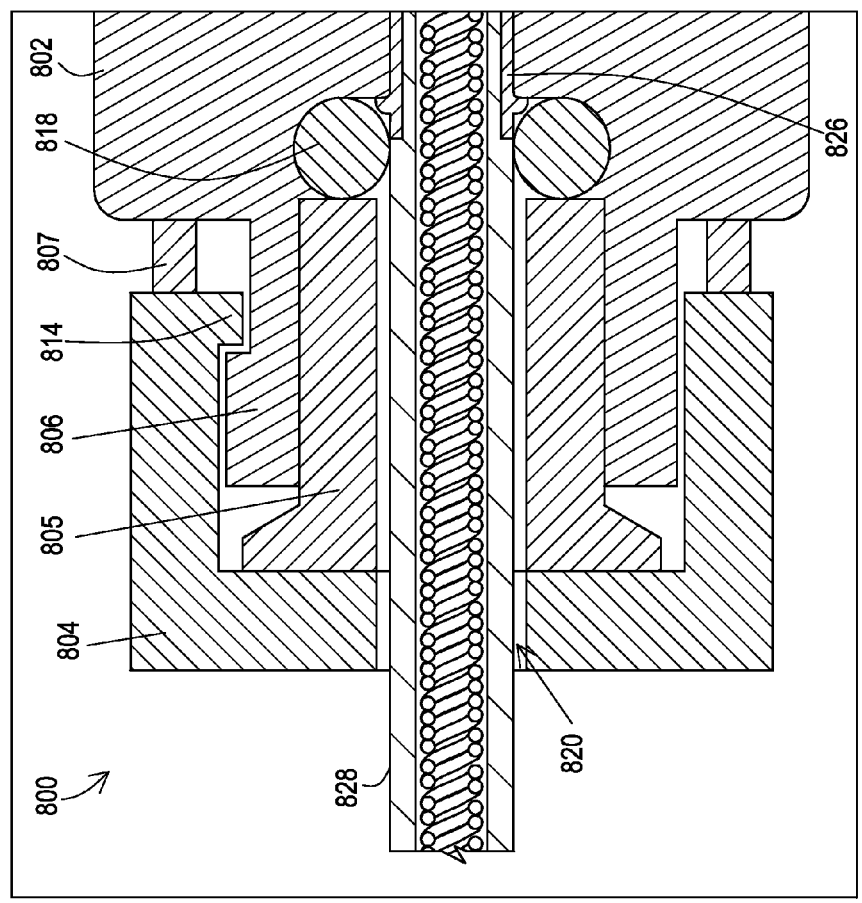
FIG. 10A shows a cross-sectional view of a seventh example that utilizes a twist lock to secure the grip and maintain fixation of a medical lead.
Figure 10D:
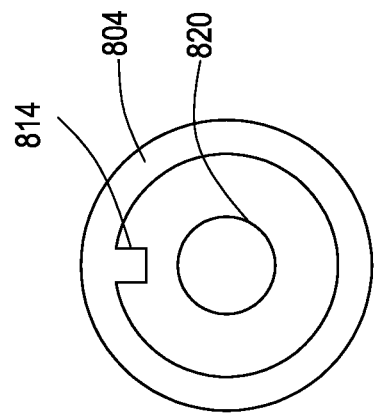
FIG. 10D shows a rear view of the grip of the example of FIG. 10A.
Figure 10C:
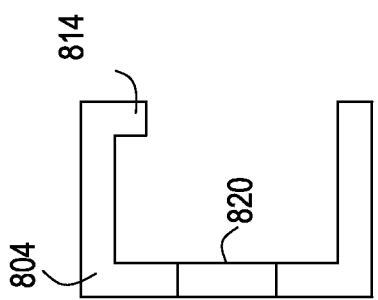
FIG. 10C shows a side cross-sectional view of the grip of the example of FIG. 10A.
Figure 10B:
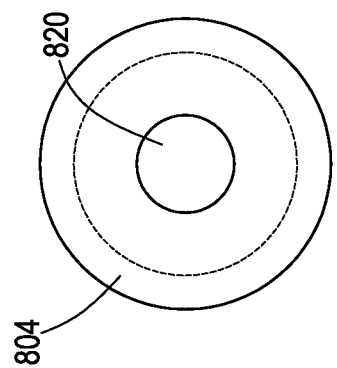
FIG. 10B shows a front view of the grip of the example of FIG. 10A.
Figure 10E:
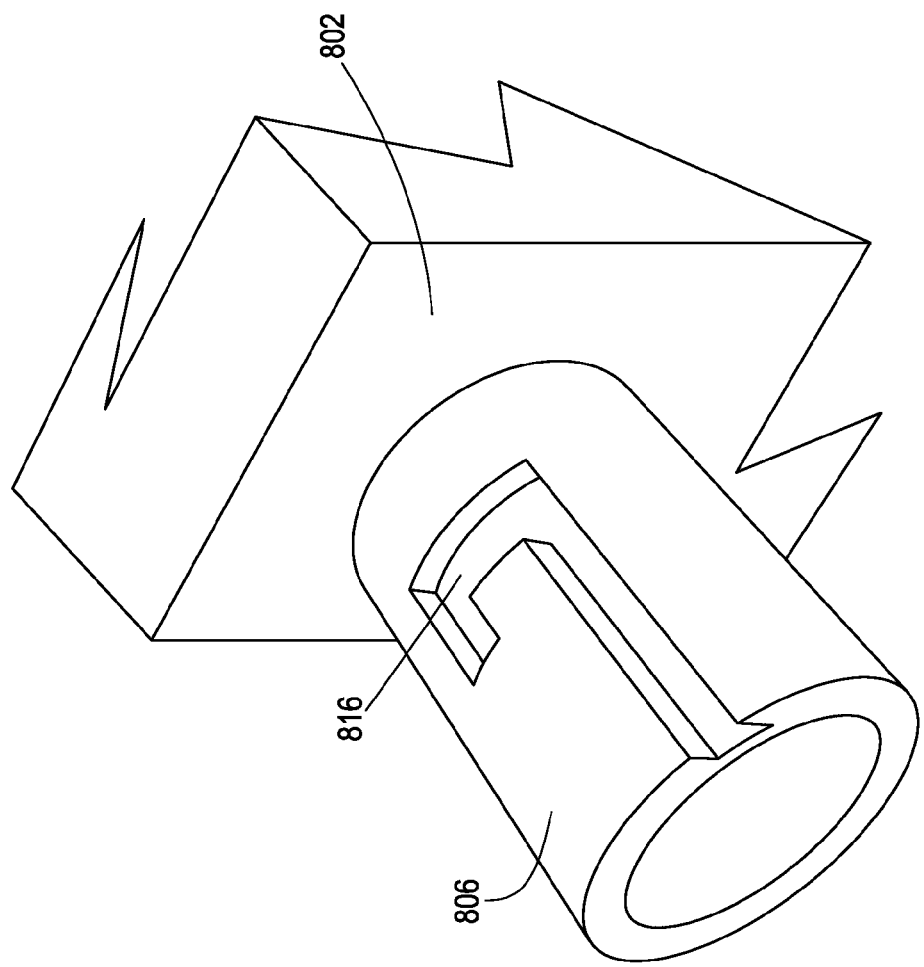
FIG. 10E shows a perspective view of the medical device of the example of FIG. 10A to further illustrate a slot that provides the twist lock in conjunction with the grip.

FIGS. 10A-10E show an example where a twist locking grip is used instead of a threaded grip. The housing 802 of the header block 800 of a medical device includes the deformable structure 818 that engages the lead 828, such as at the connector 826 to provide fixation. The translation of the grip 804 due to force by a user causes translation of the ferrule 805 which is forced into the deformable structure 818 to cause compression onto the lead 828 that passes through the bore 820. Rather than threading the grip 804 onto the nose structure 806, the grip 804 includes a protrusion 814 that engages and travels along a slot 816 present on the nose structure 806. As can be seen in FIG. 10E, the slot 816 has a turn that establishes a locked position when the protrusion 814 is forced as far as possible toward the housing 802, is then twisted as far as possible within the slot 816, and is thereafter released. There is a slight amount of over pressure applied to the deformable structure 818 during the twisting motion and then the pressure is reduced slightly to the normal lead fixation pressure once the grip 804 is released into the locked position provided by the turn in the path of slot the 816.

While the twist of the grip 804 to the locked position in the path of the slot 816 is a counter-clockwise twist as shown in FIG. 10E, it will be appreciated that the path of the slot 816 could instead provide for a clockwise twist to lock the position of the grip 804. Additionally, the provide additional back pressure on the grip 804 to further hold the grip 804 in the locked position provided by the path of the slot 816, a washer 807 may be positioned between the header block 802 and the grip 804. This washer 807 may be a lock washer, a Bellevue washer, and the like to provide the back pressure onto the grip 804. Additionally, the washer 807 may be attached to the grip 804, attached to the header block 802, or may exist as a separate object positioned between the grip 804 and header block 802. Furthermore, it will be appreciated that such a washer may be included in the prior embodiments also in order to create pressure and friction against the threaded grips in order to resist the loosening of the grips.

While embodiments have been particularly shown and described, it will be understood by those skilled in the art that various other changes in the form and details may be made therein without departing from the spirit and scope of the invention.

What is claimed is:

1. A method of fixing a proximal end of medical lead into a bore of a medical device, comprising:
    inserting the proximal end of the medical lead into the bore while a grip is coupled to the medical device; and
    transferring force from the grip that is movable relative to the bore to a deformable structure constrained within the bore by the medical device to cause compression of the deformable structure so that the deformable structure engages the lead within the bore to fix the position of the lead as the deformable structure compresses.

2. The method of claim 1, wherein transferring force from the grip to the deformable structure comprises turning of the grip so that threads of the grip that are engaged with threads of the medical device cause the grip to translate toward the deformable structure.

3. The method of claim 2, further comprising causing a mating structure on the grip to engage a mating structure on the medical device to prevent the grip from turning.

4. The method of claim 1, wherein transferring force from the grip to the deformable structure further comprises moving the grip to force a ferrule to contact and compress the deformable structure.

5. The method of claim 1, wherein transferring force from the grip to the deformable structure further comprises moving the grip into contact with the deformable structure to compress the deformable structure.

6. The method of claim 1, wherein the deformable structure is an O-ring that applies a force in a radial direction of the bore upon being compressed.

7. The method of claim 1, wherein the deformable structure is a conical structure that engages a conical portion of the medical device and that applies a force in a radial direction of the bore upon being compressed.

8. The method of claim 7, wherein the conical portion contacts a ring on the lead.

9. The method of claim 1, wherein transferring force from the grip to the deformable structure comprises forcing the grip so that a protrusion of the grip travels along a slot of the medical device and so that the grip translates toward the deformable structure and twisting the grip to cause the protrusion to follow a turn in the path that locks the grip in place.

10. An medical device, comprising:
    a header block having a bore with an engagement surface and a plurality of electrical connectors within the bore, the bore configured to receive a lead;
    a grip mechanically engaged with the engagement surface of the header block while the bore is lead-less; and
    a deformable structure that is constrained within the bore of the header block, the deformable structure providing a compression force in a radial direction of the bore when a force is applied from the grip to the deformable structure.

11. The medical device of claim 10, wherein the engagement surface is a threaded surface and wherein the grip provides a threaded surface that engages the threaded surface of the header block.

12. The medical device of claim 11, further comprising a mating structure on the grip and a mating structure on the header block, wherein the mating structure on the grip engages the mating structure on the header block to prevent the grip from turning.

13. The medical device of claim 11, wherein the engagement surface is on an exterior of a portion of the header block and the threaded surface of the grip is on an interior portion of the grip.

14. The medical device of claim 11, wherein the engagement surface is on an interior of a portion of the header block and the threaded surface of the grip is on an exterior portion of the grip.

15. The medical device of claim 10, further comprising a ferrule that is movable relative to the bore, the grip abutting the ferrule to move the ferrule when the grip is moved, the ferrule being in contact with the deformable structure.

16. The medical device of claim 10, wherein the grip contacts the deformable structure.

17. The medical device of claim 10, wherein the deformable structure is an O-ring.

18. The medical device of claim 16, wherein the deformable structure is a conical structure that engages a conical portion of the header block and that applies a force in a radial direction of the bore upon being compressed.

19. The medical device of claim 18, wherein the conical structure comprises slits.

20. The medical device of claim 10, wherein a housing of the header block is a polymer.

21. The medical device of claim 10, wherein a housing of the header block is a metal.

22. The medical device of claim 10, wherein the deformable structure contacts the lead body directly.

23. The medical device of claim 10, further comprising a metal ring on the lead and wherein the deformable structure contacts the metal ring.

24. The medical device of claim 10, wherein the header block has a second bore with a second engagement surface and a plurality of electrical connectors within the second bore;
    a second grip mechanically engaged with the second engagement surface of the header block; and
    a second deformable structure that is constrained by the header block, the deformable structure providing a compression force in a radial direction of the second bore when a force is applied from the second grip to the second deformable structure.

25. The medical device of claim 10, wherein the engagement surface comprises a slot that defines a path with a turn and wherein the grip provides a protrusion that engages the slot of the header block and moves within the slot to become locked in place.

26. A medical system, comprising:
   a medical device having a stimulation circuit and a header block, the header block having a bore with an engagement surface and a plurality of electrical connectors within the bore that are electrically coupled to the stimulation circuit;
the medical device further comprising:
   a grip mechanically engaged with the engagement surface of the header block; and
   a deformable structure that is constrained within the bore of the header block, the deformable structure providing a compression force in a radial direction of the bore when a force is applied from the grip to the deformable structure; and
   a medical lead having a lead body surrounding electrical conductors, the lead body having a proximal region that is positioned within the bore of the header block after the grip has mechanically engaged the engagement surface of the header block, the proximal region having a plurality of contacts that engage corresponding electrical connectors in the bore and engage the conductors within the lead body, the deformable structure being compressed into contact with a portion of the proximal region of the medical lead to fix the medical lead within the bore.

27. The medical system of claim 26, wherein the engagement surface is a threaded surface and wherein the grip provides a threaded surface that engages the threaded surface of the header block.

28. The medical system of claim 27, wherein the medical device further comprises a mating structure on the grip and a mating structure on the header block, wherein the mating structure on the grip engages the mating structure on the header block to prevent the grip from turning.

29. The medical system of claim 27, wherein the engagement surface is on an exterior of a portion of the header block and the threaded surface of the grip is on an interior portion of the grip.

30. The medical system of claim 27, wherein the engagement surface is on an interior of a portion of the header block and the threaded surface of the grip is on an exterior portion of the grip.

31. The medical system of claim 26, further comprising a ferrule that is movable relative to the bore, the grip abutting the ferrule to move the ferrule when the grip is moved, the ferrule being in contact with the deformable structure.

32. The medical system of claim 31, wherein the medical device includes a nose structure and wherein the ferrule comprises a collar that abuts the nose structure upon manipulation of the grip to prevent over compression of the deformable structure.

33. The medical system of claim 26, wherein the grip contacts the deformable structure.

34. The medical system of claim 26, wherein the deformable structure is an O-ring.

35. The medical system of claim 33, wherein the deformable structure is a conical structure that engages a conical portion of the header block and that applies a force in a radial direction of the bore upon being compressed.

36. The medical system of claim 35, wherein the conical structure comprises slits.

37. The medical system of claim 26, wherein a housing of the header block is a polymer.

38. The medical system of claim 26, wherein a housing of the header block is a metal.

39. The medical system of claim 26, wherein the deformable structure contacts the lead body directly.

40. The medical system of claim 26, further comprising a metal ring on the lead and wherein the deformable structure contacts the metal ring.

41. The medical system of claim 26, wherein the header block has a second bore with a second engagement surface and a plurality of electrical connectors within the second bore;
   a second grip mechanically engaged with the second engagement surface of the header block; and
   a second deformable structure that is constrained by the header block, the deformable structure providing a compression force in a radial direction of the second bore when a force is applied from the second grip to the second deformable structure.

42. The medical system of claim 26, wherein the header block includes an integral nose structure that provides the engagement surface.

43. The medical system of claim 26, wherein the deformable structure being compressed into contact with a portion of the proximal region of the medical lead creates a seal.

44. The medical system of claim 26, wherein the engagement surface comprises a slot that defines a path with a turn and wherein the grip provides a protrusion that engages the slot of the header block and moves within the slot to become locked in place.

* * * * *